(12) United States Patent
Kim et al.

(10) Patent No.: US 11,186,702 B2
(45) Date of Patent: *Nov. 30, 2021

(54) PLASTICIZER COMPOSITION AND RESIN COMPOSITION INCLUDING THE SAME

(71) Applicant: LG CHEM, LTD., Seoul (KR)

(72) Inventors: Hyun Kyu Kim, Daejeon (KR); Mi Yeon Lee, Daejeon (KR); Yun Ki Cho, Daejeon (KR); Jeong Ju Moon, Daejeon (KR); Joo Ho Kim, Daejeon (KR); Seok Ho Jeong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 53 days.

This patent is subject to a terminal disclaimer.

(21) Appl. No.: 15/580,993

(22) PCT Filed: Apr. 17, 2017

(86) PCT No.: PCT/KR2017/004118
§ 371 (c)(1),
(2) Date: Dec. 8, 2017

(87) PCT Pub. No.: WO2017/183877
PCT Pub. Date: Oct. 26, 2017

(65) Prior Publication Data
US 2018/0163018 A1 Jun. 14, 2018

(30) Foreign Application Priority Data

Apr. 22, 2016 (KR) .................. 10-2016-0049081
Apr. 13, 2017 (KR) .................. 10-2017-0047832

(51) Int. Cl.
| | | |
|---|---|---|
| C08K 5/11 | (2006.01) | |
| C08K 5/12 | (2006.01) | |
| C08K 5/1515 | (2006.01) | |
| C07C 69/75 | (2006.01) | |
| C08K 9/04 | (2006.01) | |
| C07C 67/62 | (2006.01) | |
| C08K 5/092 | (2006.01) | |
| C08K 5/00 | (2006.01) | |

(52) U.S. Cl.
CPC ............ C08K 5/12 (2013.01); C07C 67/62 (2013.01); C07C 69/75 (2013.01); C08K 5/092 (2013.01); C08K 5/11 (2013.01); C08K 5/1515 (2013.01); C08K 9/04 (2013.01); C08K 5/0016 (2013.01); C08K 2201/014 (2013.01)

(58) Field of Classification Search
CPC . C08K 5/12; C08K 5/092; C08K 5/11; C08K 5/1515; C08K 9/04; C08K 5/0016; C08K 2201/014; C07C 67/62; C07C 69/75

USPC .................................................... 524/114, 14
See application file for complete search history.

(56) References Cited

U.S. PATENT DOCUMENTS

| | | |
|---|---|---|
| 7,208,545 B1 | 4/2007 | Brunner et al. |
| 8,283,411 B2 | 10/2012 | Gosse et al. |
| 2005/0020718 A1 | 1/2005 | Gosse et al. |
| 2007/0287781 A1* | 12/2007 | Grass .................. C07C 69/67 524/308 |
| 2007/0293646 A1 | 12/2007 | Gosse et al. |
| 2008/0274364 A1 | 11/2008 | Gosse et al. |
| 2009/0291304 A1 | 11/2009 | Gosse et al. |
| 2011/0040001 A1 | 2/2011 | Gosse et al. |
| 2011/0046283 A1 | 2/2011 | Grass et al. |
| 2012/0071598 A1 | 3/2012 | Gosse et al. |
| 2012/0077914 A1 | 3/2012 | Chung et al. |
| 2013/0225737 A1 | 8/2013 | Gosse et al. |
| 2016/0326346 A1 | 11/2016 | Gourdin et al. |

FOREIGN PATENT DOCUMENTS

| | | | |
|---|---|---|---|
| CN | 101024705 A | 8/2007 | |
| CN | 103965564 A | 8/2014 | |
| EP | 0138147 A2 * | 4/1985 | ............... C08K 5/11 |
| EP | 2810982 A1 | 12/2014 | |
| JP | 2009-062394 A | 3/2009 | |
| KR | 10-2009-0038514 A | 4/2009 | |
| KR | 10-2016-0047221 A | 5/2016 | |
| KR | 10-2016-0134573 A | 11/2016 | |
| WO | 2013-004265 A | 1/2013 | |
| WO | 2013043711 A1 | 3/2013 | |
| WO | 2015-101569 A | 7/2015 | |
| WO | 2015/147300 A1 | 10/2015 | |

OTHER PUBLICATIONS

KR 20090038514 A, machine translation, EPO Espacenet. (Year: 2009).*

* cited by examiner

*Primary Examiner* — Josephine L Chang
(74) *Attorney, Agent, or Firm* — Dentons US LLP

(57) ABSTRACT

Provided is a plasticizer composition, a resin composition and a method of preparing the same. The plasticizer composition comprises two or more kinds of cyclohexane 1,4-diester-based materials; and a citrate-based material. Particularly, a plasticizer capable of improving physical properties such as plasticizer efficiency, migration, tensile strength, elongation rate, stress migration and light resistance, which are required for sheet formulations, when used as a plasticizer for a resin composition by improving poor physical properties generated due to a structural limitation thereof, and a resin composition including the same are provided.

10 Claims, 1 Drawing Sheet

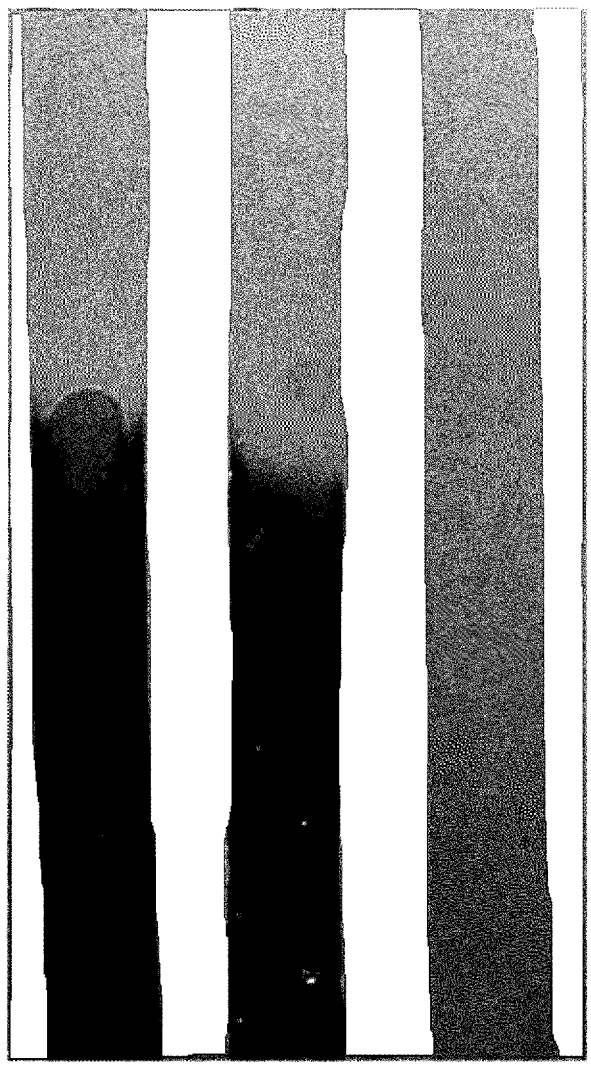

PLASTICIZER COMPOSITION AND RESIN COMPOSITION INCLUDING THE SAME

CROSS-REFERENCE TO RELATED APPLICATION

This application is a National Stage Entry of International Application No. PCT/KR2017/004118 filed on Apr. 17, 2017, and claims the benefit of Korean Application No. 10-2016-0049081, filed on Apr. 22, 2016 and Korean Patent Application No. 10-2017-0047832, filed on Apr. 13, 2017, all of which are hereby incorporated by reference in their entirety for all purposes as if fully set forth herein.

BACKGROUND

1. Field of the Invention

The present invention relates to a plasticizer composition and a resin composition comprising the same.

2. Discussion of Related Art

Conventionally, a plasticizer forms an ester through a reaction between an alcohol and a polycarboxylic acid such as phthalic acid or adipic acid. In addition, in consideration of domestic and international regulations for phthalate-based plasticizers harmful to humans, there is ongoing research on plasticizer compositions that can replace phthalate-based plasticizers such as terephthalate-, adipate-, and other polymer-based plasticizers.

Meanwhile, there is an increasing demand for environmentally friendly products relating to flooring materials, wallpaper, soft and hard sheets, etc. obtained in the plastisol industry, the calendering industry, the extruding/injecting compound industry, etc., and in order to reinforce quality characteristics, processability and productivity of each end product for such environmentally friendly products, suitable plasticizers have to be used depending on discoloration, migration, mechanical properties, etc.

Depending on properties required by industry in various areas of use, such as tensile strength, an elongation rate, light fastness, a migration property, gelability or an absorption rate, a PVC resin is mixed with a supplementary material such as a plasticizer, a filler, a stabilizer, a viscosity depressant, a dispersant, an antifoaming agent or a foaming agent.

As an example, among plasticizer compositions applicable to PVC, when di(2-ethylhexyl)terephthalate which is relatively cheap and most widely used is applied, a plasticizer exhibits high hardness or sol viscosity, a relatively low absorption rate, and poor migration and stress migration.

To improve these physical properties, a hydrogenated material of di(2-ethylhexyl)terephthalate may be considered. However, the hydrogenated material may provide improvement in plasticization efficiency, but may impart poor migration or thermal stability, and is accompanied by an increase in production cost caused by hydrogenation, and therefore it is difficult to ensure economic feasibility.

To overcome such a problem, there is a consistent demand for developing a new composition product including a material which has physical properties superior to the hydrogenated di(2-ethylhexyl)terephthalate, such as di(2-ethylhexyl) 1,4-cyclohexanoate, or a new derivative thereof, and research on developing products and their use as environmentally friendly plasticizers for vinyl chloride-based resins is progressing.

SUMMARY OF THE INVENTION

The present invention provides a plasticizer used in a resin composition, which can improve physical properties such as plasticization efficiency, migration, gelability, etc., required in formulations for a calendering sheet, plastisol, extrusion/injection compounds, etc., a method of preparing the same, and a resin composition including the same.

Specifically, based on the ideas that migration can be improved when a citrate-based plasticizer is mixed at a certain amount to solve the problems of migration and plasticization efficiency, and economic feasibility of hydrogenated di(2-ethylhexyl)terephthalate, and the use of a mixed hydrogenated composition having two or more compositions, rather than a hydrogenated single material, provides excellent plasticization efficiency and migration, an excellent plasticizer absorption rate and stress migration, the present invention is directed to providing a plasticizer composition, which includes two kinds of 1,4-cyclohexane diester-based materials and a citrate-based material.

In one aspect, according to an exemplary embodiment of the present invention, a plasticizer composition, which includes two kinds of cyclohexane 1,4-diester-based materials and a citrate-based material, is provided, and a weight ratio of the cyclohexane 1,4-diester-based materials and the citrate-based material is from 99:1 to 1:99.

The citrate-based material may include any one selected from the group consisting of hybrid C4-C10 alkyl substituted citrate-based materials and non-hybrid C4-C10 alkyl substituted citrate-based materials.

The plasticizer composition may further include an epoxidized material.

The epoxidized material may be further included at 1 to 100 parts by weight with respect to 100 parts by weight of the sum of the cyclohexane 1,4-diester-based materials and the citrate-based material.

In another aspect, according to an exemplary embodiment of the present invention, a method of preparing a plasticizer composition is provided, the method comprising: preparing a cyclohexane 1,4-diester-based material by hydrogenating a terephthalate-based material in the presence of a metal catalyst; and blending the cyclohexane 1,4-diester-based material and a citrate-based material at a weight ratio of 99:1 to 1:99 to obtain a plasticizer composition, and the terephthalate-based material is a mixture.

In still another aspect, according to an exemplary embodiment of the present invention, a resin composition which includes 100 parts by weight of a resin; and 5 to 150 parts by weight of claim 1 is provided.

The resin may include one or more selected from the group consisting of ethylene vinyl acetate, polyethylene, polypropylene, polyketone, polyvinyl chloride, polystyrene, polyurethane, and a thermoplastic elastomer.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is an image indicating the improvement in thermal resistance according to addition of an epoxidized material.

DETAILED DESCRIPTION OF EXEMPLARY EMBODIMENTS

Hereinafter, to help in understanding the present invention, the present invention will be described in further detail.

It should be noted that terms and words used herein and in the claims should not be interpreted as being limited to a conventional or literal meaning, but should be interpreted with meanings and concepts which are consistent with the technological scope of the invention based on the principle that the inventors have appropriately defined concepts of terms in order to describe the invention in the best way.

The term "butyl" used herein refers to an alkyl group having 4 carbon atoms, and includes both linear and branched chains. For example, the butyl may be n-butyl, isobutyl, or t-butyl, and preferably, n-butyl or isobutyl.

The terms "octyl" and "2-ethylhexyl" used herein refer to an alkyl group having 8 carbon atoms, and as octyl is an abbreviation of 2-ethylhexyl, may be mixed. Therefore, in some cases, these terms may mean octyl, which is a linear alkyl group, but may also be interpreted to mean 2-ethylhexyl, which is a branched alkyl group.

Plasticizer Composition

According to an exemplary embodiment of the present invention, a plasticizer composition including two or more kinds of cyclohexane 1,4-diester-based materials may be provided. Specifically, the cyclohexane 1,4-diester-based materials may be included in an amount of 1 to 99 wt %, 20 to 99 wt %, 40 to 99 wt %, 50 to 95 wt % or 60 to 90 wt % based on a total weight of the composition.

The cyclohexane 1,4-diester-based material may be a compound represented by Formula 1 below:

[Formula 1]

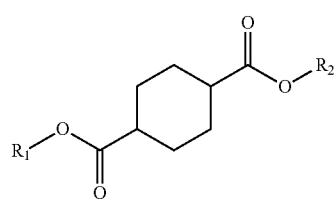

In Formula 1, $R_1$ and $R_2$ are the same as or different, and each of $R_1$ and $R_2$ may be selected from alkyl groups having 1 to 12 carbon atoms.

In the specification, the cyclohexane 1,4-diester-based material may be named dialkyl cyclohexane-1,4-diester, for example, when $R_1$ and $R_2$ are the same, and may be named alkyl($R_1$)alkyl($R_2$) cyclohexane-1,4-diester when $R_1$ and $R_2$ are different.

The cyclohexane 1,4-diester-based materials may include a mixture of two or more selected from the group consisting of butyl(2-ethylhexyl) cyclohexane-1,4-diester (1,4-BOCH), (2-ethylhexyl)isononyl cyclohexane-1,4-diester (1,4-OINCH), butyl isononyl cyclohexane-1,4-diester (1,4-BINCH), pentyl isononyl cyclohexane-1,4-diester (1,4-PINCH), isononyl(2-propylheptyl) cyclohexane-1,4-diester (1,4-IPHCH), dibutyl cyclohexane-1,4-diester (1,4-DBCH), dipentyl cyclohexane-1,4-diester (1,4-DPCH), diisononyl cyclohexane-1,4-diester (1,4-DINCH), di(2-ethylhexyl) cyclohexane-1,4-diester (1,4-DOCH), and di(2-propylheptyl) cyclohexane-1,4-diester.

In further detail, the cyclohexane 1,4-diester-based materials may include a mixture of three kinds of cyclohexane 1,4-diester-based materials. For example, the cyclohexane 1,4-diester-based materials may be a first mixture of di(2-ethylhexyl) cyclohexane-1,4-diester, butyl(2-ethylhexyl) cyclohexane-1,4-diester and dibutyl cyclohexane-1,4-diester, a second mixture of diisononyl cyclohexane-1,4-diester, butyl isononyl cyclohexane-1,4-diester and dibutyl cyclohexane-1,4-diester, a third mixture of di(2-ethylhexyl) cyclohexane-1,4-diester, (2-ethylhexyl) isononyl cyclohexane-1,4-diester and diisononyl cyclohexane-1,4-diester, a fourth mixture of di(2-propylheptyl) cyclohexane-1,4-diester, isononyl(2-propylheptyl) cyclohexane-1,4-diester and diisononyl cyclohexane-1,4-diester or a fifth mixture of dipentyl cyclohexane-1,4-diester, pentyl isononyl cyclohexane-1,4-diester and diisononyl cyclohexane-1,4-diester.

Specifically, the first to fifth mixtures may have specific composition ratios, and the first mixture may include 3.0 to 99.0 mol % of the di(2-ethylhexyl) cyclohexane-1,4-diester, 0.5 to 96.5 mol % of butyl (2-ethylhexyl) cyclohexane-1,4-diester and 0.5 to 96.5 mol % of dibutyl cyclohexane-1,4-diester, the second mixture may include 3.0 to 99.0 mol % of diisononyl cyclohexane-1,4-diester, 0.5 to 96.5 mol % of butyl isononyl cyclohexane-1,4-diester and 0.5 to 96.5 mol % of dibutyl cyclohexane-1,4-diester, the third mixture may include 3.0 to 99.0 mol % of di(2-ethylhexyl) cyclohexane-1,4-diester, 0.5 to 96.5 mol % of (2-ethylhexyl) isononyl cyclohexane-1,4-diester and 0.5 to 96.5 mol % of diisononyl cyclohexane-1,4-diester, the fourth mixture may include 3.0 to 99.0 mol % of di(2-propylheptyl) cyclohexane-1,4-diester, 0.5 to 96.5 mol % of isononyl (2-propylheptyl) cyclohexane-1,4-diester and 0.5 to 96.5 mol % of diisononyl cyclohexane-1,4-diester, and the fifth mixture may include 3.0 to 99.0 mol % of dipentyl cyclohexane-1,4-diester; 0.5 to 96.5 mol % of pentyl isononyl cyclohexane-1,4-diester and 0.5 to 96.5 mol % of diisononyl cyclohexane-1,4-diester.

The composition ratio may be a ratio of a mixed composition generated by esterification, and a composition ratio designed by further mixing a specific compound. The mixed composition ratio may be suitably controlled for desired physical properties.

As such, when the cyclohexane 1,4-diester-based materials include a mixture of two or more materials, the plasticizer composition may be improved in migration, and have considerably excellent mechanical properties and high plasticization efficiency.

In addition, according to an exemplary embodiment of the present invention, the plasticizer composition may include a citrate-based material, and the citrate-based material may include one or more compounds selected from the group consisting of hybrid C4-C10 alkyl substituted citrate-based materials and non-hybrid C4-C10 alkyl substituted citrate-based materials.

The hybrid C4-C10 alkyl substituted citrate-based materials may include, for example, a citrate having combined substituents of C4 and C8 alkyl groups such as 1,2-dibutyl 3-(2-ethylhexyl) 2-hydroxypropane-1,2,3-tricarboxylate, 1,3-dibutyl 2-(2-ethylhexyl) 2-hydroxypropane-1,2,3-tricarboxylate, 1-butyl 2,3-di(2-ethylhexyl) 2-hydroxypropane-1,2,3-tricarboxylate, or 2-butyl 1,3-di(2-ethylhexyl) 2-hydroxypropane-1,2,3-tricarboxylate; and a citrate having combined substituents of C5 and C7 alkyl groups such as 1,2-dipentyl 3-heptyl 2-hydroxypropane-1,2,3-tricarboxylate, 1,3-dipentyl 2-heptyl 2-hydroxypropane-1,2,3-tricarboxylate, 1-pentyl 2,3-diheptyl 2-hydroxypropane-1,2,3-tricarboxylate, or 2-butyl 1,3-diheptyl 2-hydroxypropane-1,2,3-tricarboxylate. In addition, a citrate having combined substituents of two alkyl groups having different quantities of carbon atoms, which are selected from 4 to 10 carbon atoms, may be applied, and the alkyl groups may be linear or branched.

The non-hybrid C4-C10 alkyl substituted citrate-based materials may be linear or branched C4 to C10 alkyl substituted citrate-based materials. For example, the linear or branched C4 to C10 alkyl substituted citrate-based materials may be tributyl citrate (TBC), tripentyl citrate (TPC), trihexyl citrate (THC), triheptyl citrate (THPC), tri(2-ethylhexyl) citrate (TOC), trinonyl citrate (TNC), and tri(2-propylheptyl) citrate (TPHC). The butyl group or nonyl group may include structural isomers thereof, and for example, the butyl group may include an isobutyl group, the octyl group may include 2-ethylhexyl group, the nonyl group may include an isononyl group, and the 2-propylheptyl group may include an isodecyl group.

Although not limited, the non-hybrid C4-C10 alkyl substituted citrate-based materials may be preferable to the hybrid alkyl substituted citrate-based material, and tributylcitrate and/or tri(2-ethylhexyl)citrate may be used a little more often.

Meanwhile, a trialkyl citrate such as the hybrid or non-hybrid alkyl substituted citrate compound, or di n-alkyl-m-alkyl citrate may be applied, and when an acetyl group is present in the citrate-based material, physical properties of the plasticizer, particularly, processability and gelability, caused by a decrease in plasticization efficiency, may be degraded.

In other words, when the citrate-based material is an acetyl citrate compound in which hydrogen of remaining hydroxyl groups, other than three ester groups, is substituted with an acetyl group, due to problems of reduced plasticization efficiency, addition of an increased amount of a plasticizer to overcome the reduced plasticization efficiency and an increased price of a product thereby, various aspects such as marketability, economic feasibility and physical properties may deteriorate.

Here, in the plasticizer composition, the upper limit of the weight ratio of the cyclohexane 1,4-diester-based materials to the citrate-based material may be 99:1, 95:5, 90:10, 85:15, 80:20, 70:30 or 60:40, and the lower limit thereof may be 1:99, 5:95, 10:90, 15:85, 20:80, 30:70 or 40:60. The weight ratio is preferably from 90:10 to 20:80, and more preferably from 90:10 to 30:70.

The plasticizer composition may include the cyclohexane 1,4-diester-based materials and the citrate-based material, and further include an epoxidized material.

The plasticizer composition including a mixture of the cyclohexane 1,4-diester-based materials and the citrate-based material may not exhibit relatively lower thermal resistance among various physical properties, and such low thermal resistance can be compensated by the addition of the epoxidized material.

An amount of the epoxidized material added to compensate the thermal resistance may be 1 to 100 parts by weight, and preferably, 5 to 80 parts by weight, with respect to 100 parts by weight of the sum of the cyclohexane 1,4-diester-based materials and the citrate-based material. When the epoxidized material is added in the above range, the thermal resistance may be compensated. But when too much of the epoxidized material is added and exceeds 100 parts by weight, relatively less of the cyclohexane 1,4-diester-based materials and the citrate-based material is included. And therefore there is a risk of fundamental physical properties of the plasticizer being degraded. For this reason, it is necessary to control the amount of the epoxidized material.

The epoxidized material may be, for example, epoxidized soybean oil, epoxidized castor oil, epoxidized linseed oil, epoxidized palm oil, an epoxidized stearate, an epoxidized oleate, an epoxidized tallate, an epoxidized linoleate or a mixture thereof. The epoxidized material is preferably epoxidized soybean oil (ESO), epoxidized linseed oil (ELO) or an epoxidized ester derivative thereof, but the present invention is not limited thereto.

Method of Preparing Plasticizer Composition

According to an exemplary embodiment of the present invention, a method of preparing a plasticizer composition includes: preparing a cyclohexane 1,4-diester-based material by hydrogenating a terephthalate-based material in the presence of a metal catalyst; and blending the cyclohexane 1,4-diester-based material and a citrate-based material at a weight ratio of 99:1 to 1:99 to obtain a plasticizer composition.

The terephthalate-based material may be prepared through direct esterification of two or more alcohols selected from the group consisting of 2-ethylhexyl alcohol, isononyl alcohol, 2-propylheptyl alcohol, butyl alcohol and isobutyl alcohol, and terephthalic acid.

The direct esterification may be performed by adding terephthalic acid to an alcohol and then reacting the resulting mixture in the presence of a catalyst under a nitrogen atmosphere; removing an unreacted alcohol and neutralizing an unreacted acid; and performing dehydration and filtration through vacuum distillation.

The alcohol may be used in the range of 150 to 500 mol %, 200 to 400 mol %, 200 to 350 mol %, 250 to 400 mol %, or 270 to 330 mol % based on 100 mol % of terephthalic acid.

Meanwhile, the catalyst may include, for example, one or more selected from acidic catalysts such as sulfuric acid, hydrochloric acid, phosphoric acid, nitric acid, para-toluenesulfonic acid, methanesulfonic acid, ethanesulfonic acid, propanesulfonic acid, butanesulfonic acid, alkyl sulfate, etc., metal salts such as aluminum sulfate, lithium fluoride, potassium chloride, cesium chloride, calcium chloride, iron chloride, aluminum phosphate, etc., metal oxides such as a heteropoly acid, etc., natural/synthetic zeolites, cation and anion exchange resins, and organic metals such as a tetra alkyl titanate and polymers thereof, etc. As a specific example, the catalyst may be a tetra alkyl titanate.

An amount of the catalyst used may depend on its kind, and for instance, the amount of a homogeneous catalyst may be in the range of 0.01 to 5 wt %, 0.01 to 3 wt %, 1 to 5 wt % or 2 to 4 wt % with respect to total 100 wt % of the reactants, and the amount of a heterogeneous catalyst may be in the range of 5 to 200 wt %, 5 to 100 wt %, 20 to 200 wt %, or 20 to 150 wt % with respect to a total amount of the reactants.

The direct esterification may be performed at 80 to 270° C., and preferably, 150 to 250° C. for 10 minutes to 10 hours, preferably, 30 minutes to 8 hours, and more preferably 1 to 6 hours, and in consideration of the boiling point of an alcohol, a terephthalate-based material may be effectively obtained in the ranges of suitable temperatures, catalysts, and time.

When the terephthalate-based material is a mixture, the cyclohexane 1,4-diester-based material may also be a mixture. Accordingly, for example, the method of the present invention may be directed to preparing a terephthalate-based material, for example, through transesterification between di(2-ethylhexyl)terephthalate and butyl alcohol; transesterification between diisononyl terephthalate and butyl alcohol; or transesterification between di(2-ethylhexyl)terephthalate and diisononyl alcohol, and transesterification between diisononyl terephthalate and 2-propylheptyl.

In addition, even when alkyl groups of the terephthalate and the alcohol are changed, the same mixture as described above may be prepared. For example, a product of the transesterification between di(2-ethylhexyl)terephthalate and diisononyl alcohol may be the same as that of the transesterification between diisononyl terephthalate and 2-ethylhexyl alcohol.

The term "transesterification" used herein refers to a reaction between an alcohol and an ester as shown in Reaction Scheme 1, in which R" of the ester is exchanged with R' of the alcohol.

[Reaction Scheme 1]

According to an exemplary embodiment of the present invention, the transesterification may produce three kinds of ester compositions according to three cases in which an alkoxide of the alcohol attacks carbons of two ester (RCOOR") groups present in an ester-based compound; an alkoxide of the alcohol attacks carbons of one ester (RCOOR") group present in an ester-based compound; and there is no reaction between an alcohol and an ester group in an ester-based compound.

In addition, compared to an acid-alcohol esterification, the transesterification does not cause water contamination, and may solve problems caused by the use of an acidic catalyst because of proceeding without a catalyst.

For example, the di(2-ethylhexyl) terephthalate and the butyl alcohol may generate a mixture of di(2-ethylhexyl) terephthalate, butyl(2-ethylhexyl) terephthalate and dibutyl terephthalate by the transesterification, and these three kinds of terephthalates may be formed at 3.0 to 70 wt %, 0.5 to 50 wt %, and 0.5 to 85 wt %, specifically, 10 to 50 wt %, 0.5 to 50 wt %, and 35 to 80 wt %, respectively, with respect to a total weight of the mixture. Within these ranges, a terephthalate-based material (mixture) having high process efficiency and excellent processability and an excellent absorption rate may be obtained.

In addition, a composition ratio of the mixture prepared by the transesterification may be controlled according to an amount of the alcohol added.

The amount of the alcohol added may be 0.1 to 89.9 parts by weight, specifically, 3 to 50 parts by weight, and more specifically 5 to 40 parts by weight with respect to 100 parts by weight of the terephthalate-based material.

As a larger amount of the alcohol is added, a mole fraction of the terephthalate compound participating in the transesterification is higher, and therefore, the amounts of the products, which are two terephthalate compounds, in the mixture may increase, and correspondingly, an amount of the unreacted terephthalate compound present may tend to be reduced.

According to an exemplary embodiment of the present invention, a molar ratio of the reactants, which are the terephthalate compound and the alcohol may be, for example, 1:0.005 to 5.0, 1:0.05 to 2.5, or 1:0.1 to 1.0, and within the range, an ester-based plasticizer composition exhibiting high process efficiency and an excellent effect of improving processability may be obtained.

However, the composition ratio of the mixture of three kinds of terephthalates is not limited to the above range, and any one of the three kinds of terephthalates may be further added to change the composition ratio. Available mixed composition ratios are as described above.

The ester-based composition prepared through the transesterification may include all of a single attack ester compound, a dual attack ester compound, and reaction residual ester compound, and a composition ratio of the ester-based composition may be controlled according to the amount of the alcohol added.

The amount of the alcohol added may be 0.1 to 89.9 parts by weight, specifically 3 to 50 parts by weight, and more specifically 5 to 40 parts by weight with respect to 100 parts by weight of the terephthalate.

In the terephthalate-based material, as a larger amount of the alcohol is added, a mole fraction of the terephthalate participating in the transesterification may increase. Accordingly, in the plasticizer composition, amounts of the terephthalate produced by attacking only one ester group and the terephthalate produced by attacking two ester groups may increase.

In addition, in comparison, an amount of the unreacted residual terephthalate present may tend to be reduced.

A molar ratio of the terephthalate and the alcohol may be, for example, 1:0.005 to 5.0, 1:0.05 to 2.5, or 1:0.1 to 1.0, and within the range, a terephthalate-based material capable of providing a plasticizer composition which has high process efficiency and an excellent effect of improving processability may be obtained.

The transesterification may be performed at a reaction temperature of 120 to 190° C., preferably 135 to 180° C., and more preferably 141 to 179° C. for 10 minutes to 10 hours, preferably 30 minutes to 8 hours, and more preferably 1 to 6 hours. Within the above temperature and time ranges, a mixture of terephthalate-based materials at a desired composition ratio may be effectively obtained. Here, the reaction time may be calculated from the point of time to reach the reaction temperature after reactants are heated.

The transesterification may be performed without a catalyst, but in some cases, may be performed under an acidic catalyst or metal catalyst, which provides an effect of reducing the reaction time.

The acidic catalyst may be, for example, sulfuric acid, methanesulfonic acid or p-toluenesulfonic acid, and the metal catalyst may be, for example, an organic metal catalyst, a metal oxide catalyst, a metal salt catalyst or a metal itself.

The metal component may include, for example, any one or a mixture of two or more selected from the group consisting of tin, titanium and zirconium.

In addition, according to an exemplary embodiment of the present invention, the method may further include removing an unreacted alcohol and a reaction by-product such as an ester-based compound through distillation after the transesterification.

The distillation may be, for example, two-step distillation for separating the alcohol and the reaction by-product using a difference in boiling point.

In another example, the distillation may be mixed distillation. In this case, a desired composition ratio of an ester-based plasticizer composition may be relatively and stably ensured. The mixed distillation refers to simultaneous distillation of butanol and a reaction by-product.

The hydrogenation may be conversion of a terephthalate-based material into a cyclohexane 1,4-diester-based material by hydrogenating the terephthalate-based material, which may be a single compound or a mixture thereof, in the presence of a metal catalyst.

The hydrogenation may be a reaction for eliminating the aromaticity of benzene rings of the terephthalate-based materials by adding hydrogen in the presence of a metal catalyst, which may be a kind of reduction.

The hydrogenation is for synthesizing a cyclohexane 1,4-diester-based material by a reaction between the terephthalate-based material and hydrogen in the presence of a metal catalyst, and conditions for this reaction may include all conventional reaction conditions for hydrogenating only a benzene ring without affecting carbonyl groups substituted in the benzene.

The hydrogenation may be performed with an additional organic solvent such as ethanol or the like, but the present invention is not limited thereto. The metal catalyst may be an Rh/C catalyst, a Pt catalyst, a Pd catalyst or the like, which is generally used to hydrogenate a benzene ring, and any one capable of being used in the hydrogenation may be used without limitation.

For example, in the hydrogenation, a pressure for adding hydrogen may be approximately 3 to 15 MPa, and the reaction may be performed for approximately 2 to 10 hours at approximately 80 to 200° C.

The above-described reaction may be an example, and a final hydrogenated cyclohexane 1,4-diester-based material may be prepared as a mixed cyclohexane 1,4-diester-based composition hydrogenated by transesterification using an alcohol after a single hydrogenated cyclohexane 1,4-diester-based material is previously prepared by hydrogenation.

In other words, the final product may be prepared by an either way of hydrogenation after direct esterification and/or transesterification using terephthalic acid and/or a terephthalate or preparation of a hydrogenated mixture through transesterification after hydrogenation of a terephthalate prepared by esterification.

Meanwhile, the final hydrogenated mixed composition of three materials prepared by transesterification may generally include two kinds of materials which have the same alkyl groups of a diester and one kind of material which has different alkyl groups of a diester. Here, the kind of material which has different alkyl groups of a diester may serve as a main factor affecting physical properties of a plasticizer, but it may be commercially and technically impossible to separate these materials.

For example, while it is possible to prepare each of the materials having the same alkyl groups binding to the diesters at the 1 and 4-positions as a single material through direct esterification, a material having different alkyl groups binding to the diesters at the 1 and 4-positions of a cyclohexane is prepared only by transesterification. In this case, it is impossible to separate only the material with different alkyl groups of a diester, and even if possible, the material may be separated in only a very small amount through excessive repetition at the laboratory level.

Therefore, as an alternative, a method of controlling the number of carbon atoms of the alkyl groups or the composition ratio of the three materials in the final composition so as to exhibit optimal physical properties may be applied.

In the blending, a cyclohexane 1,4-diester-based material obtained by conversion of the terephthalate-based material through hydrogenation may be blended with a citrate-based material at a weight ratio of 1:99 to 99:1, thereby preparing the plasticizer composition, and the cyclohexane 1,4-diester-based material may depend on whether the terephthalate-based material is a single compound or a mixture thereof, and thus can be a single compound or a mixture thereof.

Amounts, kinds, and mixing ratio of the cyclohexane 1,4-diester-based material and the citrate-based material, which are mixed in the blending have been described above, and thus the descriptions thereof will be omitted.

After the blending, the method may further include adding an epoxidized material. An amount and kind of the epoxidized material to be further added have been described above, and thus the descriptions thereof will be omitted.

The above-described direct esterification and transesterification may be used to prepare the above-described hybrid or non-hybrid citrate compound. In this case, like the cyclohexane 1,4-diester-based material, a citrate-based material may also be prepared as a mixed composition prepared at a predetermined ratio, and a composition ratio of the mixture produced may be controlled by the adjustment of a amount of an alcohol as a reaction raw material. Alternatively, when a citrate compound is prepared by direct esterification or transesterification, the same process as described in the preparation of the terephthalate-based material may be applied.

According to another exemplary embodiment of the present invention, a resin composition including the above-described plasticizer composition and a resin is provided.

The resin may be any resin known in the art. For example, the resin may be a mixture of one or more selected from the group consisting of ethylene vinyl acetate, polyethylene, polypropylene, polyvinyl chloride, polystyrene, polyurethane, a thermoplastic elastomer and polylactic acid, but the present invention is not limited thereto.

The plasticizer composition may be included at 5 to 150 parts by weight based on 100 parts by weight of the resin.

However, depending on a method of processing the resin composition, a amount of the plasticizer may be changed, and in the case of a resin subjected to melt processing such as extrusion, injection or calendering, the plasticizer may be included at 5 to 100 parts by weight, 5 to 60 parts by weight, or 5 to 50 parts by weight with respect to 100 parts by weight of the resin.

In addition, in the case of a resin subjected to plastisol processing such as spread coating, spray coating or dip coating, the plasticizer may be included at 30 to 150 parts by weight, 40 to 130 parts by weight, or 60 to 120 parts by weight.

The resin composition may further include a filler. The filler may be included at 0 to 300 parts by weight, preferably, 50 to 200 parts by weight, and more preferably, 100 to 200 parts by weight based on 100 parts by weight of the resin.

The filler may be any filler known in the art without particular limitation. For example, the filler may be a mixture of one or more selected from silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate and barium sulfate.

In addition, the resin composition may further include other additives such as a stabilizer, etc. as needed. Each of the additives such as a stabilizer, etc. may be, for example, included at 0 to 20 parts by weight, and preferably 1 to 15 parts by weight based on 100 parts by weight of the resin.

The stabilizer may be a calcium-zinc (Ca—Zn)-based stabilizer such as a calcium-zinc composite stearate (salt) or the like, but the present invention is not limited thereto.

The resin composition may be applied to all of resins used in melt processing and plastisol processing, and for example, may be applied to a compound field such as extrusion or injection, the calendering field and the plastisol field, and products prepared by such processing may be, for example, all kinds of wires, flooring materials, interior materials for automobile, films, sheets, wallpaper, toys, etc.

EXAMPLES

Hereinafter, to explain the present invention in detail, the present invention will be described in detail with reference to examples. However, examples according to the present invention may be modified in a variety of different forms, and the scope of the present invention should not be construed as being limited to the examples to be described below. The exemplary embodiments of the present invention are provided for those of ordinary skill in the art to more fully understand the present invention.

Preparation Example 1: Preparation of Hydrogenated Mixture of DEHTP/BEHTP/DBTP

1) Esterification 2000 g of dioctylterephthalate (DOTP) and 340 g of n-butanol (17 parts by weight of 100 parts by weight of DOTP) were added into a reaction vessel equipped with an agitator, a condenser and a decanter to allow transesterification for 2 hours at a reaction temperature of 160° C. in a nitrogen atmosphere, thereby obtaining an ester-based plasticizer composition which includes dibutyl terephthalate (DBTP), butyl isononyl terephthalate (BINTP) and diisononyl terephthalate (DINTP) at 4.0 wt %, 35.0 wt % and 61.0 wt %, respectively.

The reaction product was subjected to mixed distillation to remove butanol and 2-ethylhexyl alcohol, resulting in preparation of a mixed composition.

2) Hydrogenation 1000 g of the composition produced by the esterification and 20 g of a ruthenium catalyst (N.E CHEMCAT) were added as raw materials into 1.5 L high-pressure reaction vessel, and hydrogen was added under a pressure of 8 MPa to perform hydrogenation at 150° C. for 3 hours, and then the reaction was completed. After the reaction, the catalyst was filtered and a conventional purification process was performed, thereby preparing a hydrogenated mixed composition with a yield of 99%.

Preparation Example 2: Preparation of Hydrogenated Mixture of DINTP/EHINTP/DEHTP 1) Esterification 498.0 g of purified terephthalic acid (PTA), 975 g of 2-ethylhexyl alcohol ((2-EH); a molar ratio of PTA:2-EH—(1.0):(2.5)) and 216.5 g of isononyl alcohol ((INA); a molar ratio of PTA:INA—(1.0):(0.5)) were added into a 4-neck 3 L reaction vessel equipped with a cooler, a condenser, a decanter, a reflux pump, a temperature controller, an agitator, etc., 1.54 g of a titanium-based catalyst (tetra isopropyl titanate (TIPT); 0.31 parts by weight with respect to 100 parts by weight of PTA) was added as a catalyst, and a temperature was slowly increased to approximately 170° C. At approximately 170° C., water was generated, and esterification was performed for approximately 4.5 hours while a nitrogen gas was continuously added at a reaction temperature of approximately 220° C. under atmospheric pressure, and then terminated when an acid value reached 0.01.

After the reaction, distillation extraction was performed for 0.5 to 4 hours under reduced pressure to remove unreacted raw materials. To remove unreacted raw materials to a predetermined amount level or less, steam extraction was performed using steam for 0.5 to 3 hours under reduced pressure, and neutralization was performed using an alkali solution after a reaction solution was cooled to approximately 90° C. Additionally, washing may be carried out, and then the reaction solution was dehydrated to remove moisture. A filtering material was input into the dehydrated reaction solution, after stirring for a predetermined time and filtering, a mixed composition was finally obtained.

2) Hydrogenation

A hydrogenated mixed composition was prepared by hydrogenating the mixed composition in the same manner as described in Preparation Example 1.

Preparation Example 3: Preparation of Hydrogenated Mixture of DINTP/BINTP/DBTP

A hydrogenated mixed composition was obtained by esterification and hydrogenation in the same manner as described in Preparation Example 2, except that, instead of the isononyl alcohol and the 2-ethylhexyl alcohol used in the esterification in Preparation Example 2, isononyl alcohol and butyl alcohol were used.

Preparation Example 4: Preparation of Hydrogenated Mixture of DINTP/PHINTP/DPHTP A hydrogenated mixed composition was obtained by esterification and hydrogenation in the same manner as described in Preparation Example 2, except that, instead of the isononyl alcohol and the 2-ethylhexyl alcohol used in the esterification in Preparation Example 2, isononyl alcohol and 2-propylheptyl alcohol were used.

Preparation Example 5: Preparation of TBC

Finally, 706 g of tributyl citrate (yield: 98%) was obtained using 384 g of citric acid and 580 g of butanol as reaction raw materials.

Preparation Example 6: Preparation of TOC

Finally, 1029 g of tri-2-ethylhexyl citrate (yield: 98%) was obtained using 384 g of citric acid and 1014 g of 2-ethylhexanol as reaction raw materials.

Preparation Example 7: Preparation of TiNC

Finally, 1111 g of triisononyl citrate (yield: 98%) was obtained using 384 g of citric acid and 1123 g of isononanol as reaction raw materials.

Preparation Example 8: Preparation of TPHC

Finally, 1,200 g of tri(2-propylheptyl) citrate (yield: 98%) was obtained using 384 g of citric acid and 1,234 g of 2-propylheptanol as reaction raw materials.

Preparation Example 9: Preparation of BOC

Transesterification was performed using 1000 g of TOC prepared in Preparation Example 6 and 300 g of n-butanol as reaction raw materials, and thus 840 g of butyloctyl citrate was finally obtained. For reference, the product was a composition, which includes BOC in which two butyl groups are bound, BOC in which one butyl group is bound and TOC in which no butyl group is bound as main components at approximately 20 wt %, 50 wt % and 30 wt %, respectively, distinguished by alkyl groups binding to three ester groups of the citrate compound.

Examples 1 to 10 and Comparative Examples 1 to 5

Compositions of the Examples and Comparative Examples are shown in Table 1 below.

TABLE 1

|  | Hydrogenated mixed composition | Citrate-based material | Mixing ratio |
|---|---|---|---|
| Example 1 | Preparation Example 1 | TBC | 7:3 |
| Example 2 | Preparation Example 1 | TBC | 3:7 |
| Example 3 | Preparation Example 1 | TOC | 8:2 |
| Example 4 | Preparation Example 2 | BOC | 7:3 |
| Example 5 | Preparation Example 2 | TOC | 2:8 |
| Example 6 | Preparation Example 2 | TPHC | 6:4 |
| Example 7 | Preparation Example 3 | TINC | 6:4 |
| Example 8 | Preparation Example 3 | TBC | 5:5 |
| Example 9 | Preparation Example 4 | TOC | 5:5 |
| Example 10 | Preparation Example 4 | TBC | 5:5 |
| Comparative Example 1 | 1,4-DEHCH | TBC | 7:3 |
| Comparative Example 2 | 1,4-DBCH | TOC | 6:4 |
| Comparative Example 3 | 1,2-DINCH | TBC | 7:3 |
| Comparative Example 4 | Preparation Example 3 | — | |
| Comparative Example 5 | — | TOC | |

Examples 11 and 12

To confirm the improvement in thermal resistance using an epoxidized material, Examples 11 and 12 are composed as shown in Table 2 below.

TABLE 2

| Classification | Hydrogenated mixed composition | Citrate-based material | Mixing ratio |
|---|---|---|---|
| Example 11 | Example 1 | ESO | 8:2 |
| Example 12 | Example 4 | ESO | 7:3 |

Experimental Example 1: Evaluation of Physical Properties

Experimental specimens were prepared using the plasticizer compositions of the Examples and Comparative Examples described in Tables 1 and 2.

Each specimen was prepared, according to ASTM D638, by mixing 40 parts by weight of each of the plasticizer compositions of Examples 1 to 10 and Comparative Examples 1 to 5, and 3 parts by weight of a stabilizer (BZ-153T) with 100 parts by weight of PVC (LS100S) using a 3 L super mixer at 98° C. and 700 rpm, forming a 5-mm sheet by roll milling at 160° C. for 4 minutes, performing pressing at 180° C. under low pressure for 2.5 minutes, and under high pressure for 2 minutes, and then forming 1 T and 3 T sheets. Physical properties of each specimen were evaluated by the test items listed below, and the results are summarized in Tables 3 and 4 below.

<Test Items>

Measurement of Hardness

According to ASTM D2240, Shore (Shore "A") hardness was measured at 25° C. under 3 T and 10 s conditions.

Measurement of Tensile Strength

According to ASTM D638, each specimen was pulled at a cross head speed of 200 mm/min (1 T) using a tensile testing instrument (U.T.M, Manufacturer; Instron, Model No.: 4466), and a position at which the specimen was broken was detected. A tensile strength was calculated as follows:

Tensile strength $(kgf/mm^2)$ = Load value (kgf)/Thickness (mm)×Width (mm)

Measurement of Elongation Rate

According to ASTM D638, each specimen was pulled at a cross head speed of 200 mm/min (1 T) using the U.T.M, and a position at which the specimen was broken was detected. An elongation rate was calculated as follows:

Elongation rate (%) = Length after elongation/Initial length×100

Measurement of Migration Loss

An experimental specimen having a thickness of 2 mm or more was obtained according to KSM-3156, and following attachment of PS plates to both sides of the specimen, a weight of 1 $kgf/cm^2$ was applied to the specimen. The specimen was put in a forced convection drying oven (80° C.) for 72 hours, and cooled at room temperature for 4 hours. Then, after the PSs attached to both sides of the specimen were removed, a weight was measured before and after the specimen was put in the oven and thus a migration loss was calculated by the equation as follows:

Migration loss (%) = [(Initial weight of specimen at room temperature−Weight of specimen after being put into oven)/Initial weight of specimen at room temperature]×100

Measurement of Volatile Loss

The prepared specimen was processed at 80° C. for 72 hours, and a weight of the specimen was measured as follows:

Volatile loss (%) = [(Weight of initial specimen−Weight of specimen after processed)/Weight of initial specimen]×100

Stress Test

A stress test was performed by leaving the specimen at room temperature for predetermined time, and a degree of migration (leaking degree) was observed and quantified. A value closer to 0 indicates a superior property and a value closer to 3 indicates a poor property.

Thermal Stability Test

A 0.5 T specimen prepared through roll-milling was moved at a rate of 10 mm/25 seconds in a 220° C. Mathis oven to test thermal stability of the specimen according to high temperature contact.

TABLE 3

| Classification | Hardness (Shore "A") | Tensile strength $(kg/cm^2)$ | Elongation rate (%) | Migration loss (%) | Volatile loss (%) | Stress test |
|---|---|---|---|---|---|---|
| Example 1 | 82.5 | 211.7 | 296.2 | 1.56 | 3.10 | 0 |
| Example 2 | 78.5 | 215.2 | 287.1 | 1.89 | 3.51 | 0 |
| Example 3 | 85.0 | 221.6 | 292.8 | 1.31 | 1.84 | 0 |
| Example 4 | 85.0 | 232.2 | 307.7 | 1.60 | 1.95 | 0 |
| Example 5 | 88.0 | 228.5 | 283.1 | 0.50 | 0.54 | 0.5 |
| Example 6 | 86.0 | 221.1 | 296.7 | 1.87 | 0.87 | 1.0 |
| Example 7 | 86.0 | 235.1 | 301.5 | 1.55 | 0.35 | 0.5 |
| Example 8 | 84.0 | 217.0 | 284.6 | 1.90 | 2.14 | 0.5 |
| Example 9 | 85.5 | 229.7 | 288.5 | 1.62 | 0.39 | 0.5 |
| Example 10 | 82.0 | 220.4 | 278.1 | 1.45 | 2.02 | 0.5 |
| Comparative Example 1 | 85.5 | 204.5 | 256.4 | 2.28 | 3.05 | 0.5 |
| Comparative Example 2 | 88.0 | 207.1 | 223.1 | 1.50 | 1.32 | 1.0 |
| Comparative Example 3 | 85.0 | 210.8 | 266.7 | 2.40 | 1.66 | 1.0 |
| Comparative Example 4 | 87.0 | 201.3 | 221.0 | 2.86 | 1.56 | 2.0 |
| Comparative Example 5 | 92.0 | 189.5 | 201.3 | 0.47 | 0.47 | 1.5 |

TABLE 4

| Classification | Hardness (Shore "A") | Tensile strength (kg/cm²) | Elongation rate (%) | Migration loss (%) | Volatile loss (%) | Stress test |
|---|---|---|---|---|---|---|
| Example 11 | 83.5 | 235.1 | 307.5 | 1.20 | 2.66 | 0 |
| Example 12 | 86.5 | 298.0 | 314.2 | 0.84 | 1.03 | 0 |

Referring to Table 3, in Comparative Example 1 to 3 in which the cyclohexane 1,4-diester-based material is a single material, compared to the Examples, it can be seen that the elongation rate is considerably low, and the tensile strength is also low. In addition, in Comparative Examples 4 and 5 that do not include any one of the citrate-based material or the cyclohexane 1,4-diester-based material, it can be confirmed that a somewhat high hardness adversely affects the plasticization efficiency, and the tensile strength and the elongation rate are very poor.

Consequently, in all aspects of the mechanical properties (the tensile strength and the elongation rate), physical properties relating to the total weight of a plasticizer (migration loss and volatile loss) and processability (hardness), it can be confirmed that, to prepare a resin having satisfactory physical properties, the cyclohexane 1,4-diester-based material is preferably used as a mixed composition, and mixed with the citrate-based material.

In addition, referring to Table 4, it can be confirmed that Examples 11 and 12 in which epoxidized soybean oil is added to Examples 1 and 4 have low volatile loss and migration loss, and improved mechanical properties such as the tensile strength, the elongation rate, etc.

Further, referring to FIG. 1, while it can be confirmed that, in Examples 1 and 4 in which the epoxidized material is not added, the specimen was burned and appeared almost black, in Example 11, almost no discoloration was visually detected, and therefore the thermal stability can be improved by addition of the epoxidized material.

That is, it can be concluded that all physical properties are improved when the epoxidized material is mixed at 10 parts by weight or more to serve as a "plasticizer," not as a subsidiary stabilizer.

A plasticizer composition according to an exemplary embodiment of the present invention, when used in a resin composition, can provide excellent physical properties such as migration resistance, volatility resistance, etc., as well as excellent plasticization efficiency, tensile strength and an excellent elongation rate.

While the present invention has been described in detail with reference to exemplary embodiments of the present invention, it should be understood to those of ordinary skill in the art that the scope of the present invention is not limited thereto, but also includes various forms of modification and alternation based on the fundamental ideas of the present invention defined by the accompanying claims.

What is claimed is:

1. A plasticizer composition, comprising:
    a first mixture of di(2-ethylhexyl) cyclohexane-1,4-diester, butyl(2-ethylhexyl) cyclohexane-1,4-diester, and dibutyl cyclohexane-1,4-diester; and
    a citrate-based material,
    wherein a weight ratio of the cyclohexane 1,4-diester-based materials and the citrate-based material is from 80:20 to 20:80; and
    wherein the citrate-based material is a citrate in which an acetyl group is not included, and is selected from the group consisting of tributyl citrate (TBC) and tri(2-ethylhexyl) citrate (TOC).

2. The plasticizer composition of claim 1, wherein the weight ratio of the cyclohexane 1,4-diester-based materials and the citrate-based material is from 80:20 to 50:50.

3. The plasticizer composition of claim 2, wherein the weight ratio of the cyclohexane 1,4-diester-based materials and the citrate-based material from 80:20 to 60:40.

4. The plasticizer composition of claim 1, further comprising:
    an epoxidized material.

5. The plasticizer composition of claim 4, wherein the epoxidized material is further comprised in an amount of 1 to 100 parts by weight based on 100 parts by weight of the sum of the cyclohexane 1,4-diester-based materials and the citrate-based material.

6. The plasticizer composition of claim 4, wherein the epoxidized material comprises one or more selected front the group consisting of epoxidized soybean oil, epoxidized castor oil, epoxidized linseed oil, epoxidized palm oil, an epoxidized stearate, an epoxidized oleate, an epoxidized tallate and an epoxidized linoleate.

7. A resin composition comprising:
    100 parts by weight of a resin; and 5 to 150 parts by weight of the plasticizer composition of claim 1.

8. The resin composition of claim 7, wherein the resin comprises one or more selected from the group consisting of ethylene vinyl acetate, polyethylene, polypropylene, polyketone, polyvinyl chloride, polystyrene, polyurethane, and a thermoplastic elastomer.

9. A plasticizer composition, comprising:
    a second mixture of diisononyl cyclohexane-1,4-diester, butyl isononyl cyclohexane-1,4-diester, and dibutylcyclohexane-1,4-diester; and
    a citrate-based material,
    wherein a weight ratio of the cyclohexane 1,4-diester-based materials and the citrate-based material is from 80:20 to 20:80; and
    wherein the citrate-based material is a tributyl citrate (TBC).

10. A plasticizer composition, comprising:
    a fourth mixture of di(2-propylheptyl) cyclohexane-1,4-diester, isononyl(2-propylheptyl) cyclohexane-1,4-diester, and diisononyl cyclohexane-1,4-diester; and
    a citrate-based material,
    wherein a weight ratio of the cyclohexane 1,4-diester-based materials and the citrate-based material is from 80:20 to 20:80; and
    wherein the citrate-based material is a citrate in which an acetyl group is not included, and is selected from the group consisting of tributyl citrate (TBC) and tri(2-ethylhexyl) citrate (TOC).

* * * * *